(12) United States Patent
Gaston

(10) Patent No.: US 6,695,855 B1
(45) Date of Patent: Feb. 24, 2004

(54) DEVICE FOR TREATING A PROLAPSE BY VAGINAL SUSPENSION

(75) Inventor: Richard-Pierre Gaston, Bordeaux-Cauderan (FR)

(73) Assignee: Sofradim Production, Trevoux (FR)

( * ) Notice: Subject to any disclaimer, the term of this patent is extended or adjusted under 35 U.S.C. 154(b) by 0 days.

(21) Appl. No.: 09/937,342

(22) PCT Filed: Apr. 6, 2000

(86) PCT No.: PCT/FR00/00874
§ 371 (c)(1),
(2), (4) Date: Nov. 20, 2001

(87) PCT Pub. No.: WO00/64370
PCT Pub. Date: Nov. 2, 2000

(30) Foreign Application Priority Data

Apr. 27, 1999 (FR) .............................. 99 05487

(51) Int. Cl.[7] .............................. A61B 17/08; A61F 2/00
(52) U.S. Cl. .......................................... 606/151; 600/29
(58) Field of Search ................................ 606/232, 151; 600/29, 30, 37

(56) References Cited

U.S. PATENT DOCUMENTS

| | | | | |
|---|---|---|---|---|
| 5,036,867 A | * | 8/1991 | Biswas | 128/885 |
| 5,441,508 A | * | 8/1995 | Gazielly et al. | 606/151 |
| 5,972,022 A | * | 10/1999 | Huxel | 606/215 |
| 6,042,534 A | * | 3/2000 | Gellman et al. | 600/30 |
| 6,042,592 A | * | 3/2000 | Schmitt | 606/151 |
| 6,110,101 A | * | 8/2000 | Tihon et al. | 600/37 |
| 6,287,316 B1 | * | 9/2001 | Agarwal et al. | 606/151 |
| 6,328,686 B1 | * | 12/2001 | Kovac | 600/30 |

FOREIGN PATENT DOCUMENTS

| | | |
|---|---|---|
| EP | 0 248 544 A1 | 12/1987 |
| WO | WO 97/13465 | 4/1997 |
| WO | WO 98/35632 | 8/1998 |

* cited by examiner

Primary Examiner—Michael H. Thaler
Assistant Examiner—P Roberts
(74) Attorney, Agent, or Firm—Oliff & Berridge, PLC

(57) ABSTRACT

The inventive device consist of a unit (1) formed by an elongated part (5) made from a flexible pierced material, a suture (6) linked to a longitudinal extremity of said part (5) and a suture needle (7) joined to said suture (6). The part (5) is long enough to enable posterior suspension of the vagina (2) at the promontory (3), i.e. the front upper part of the sacrum. At the extremity which is joined to the suture, the part (5) comprises the following: (i) a distal portion (5c) being of a sufficient width that it can cover at least a large part of the posterior part of the wall of the vagina (2) and (ii) a cut-out (5d) which is rounded and fitted to the side edge of the distal extremity (5e), whereby said cut-out (5d) has dimensions that are such to enable the part (5) to engaged around the base of the wall of the vagina (2) on at least a large part of the lower half of said wall. The suture (6) is connected to the base in such a way that it is offset sidewise in relation to the cut (5d).

18 Claims, 2 Drawing Sheets

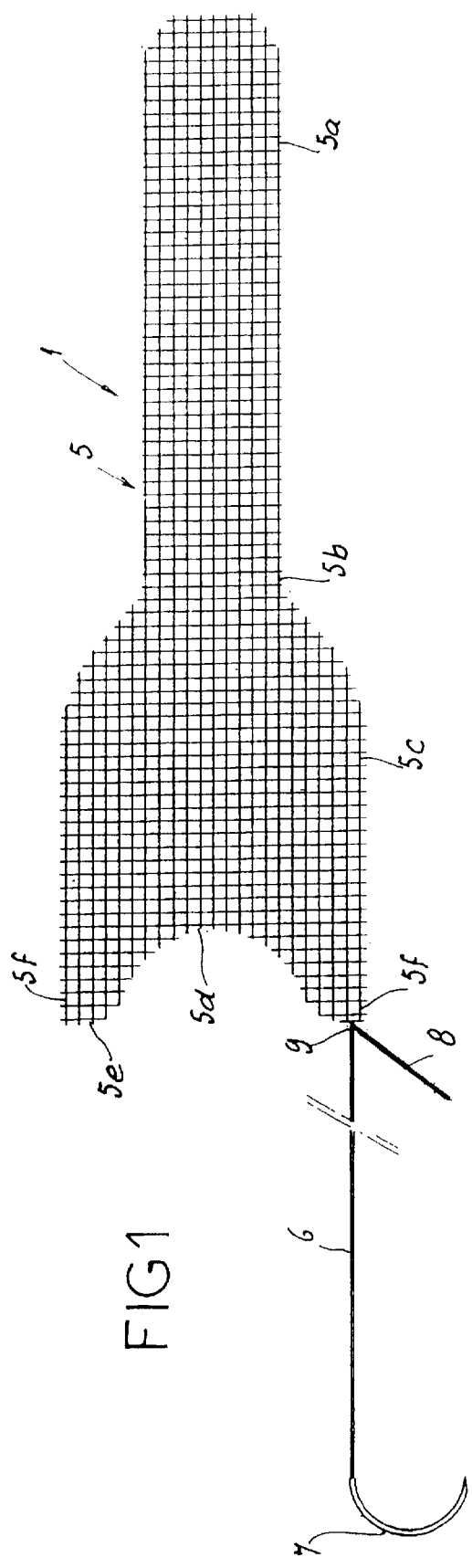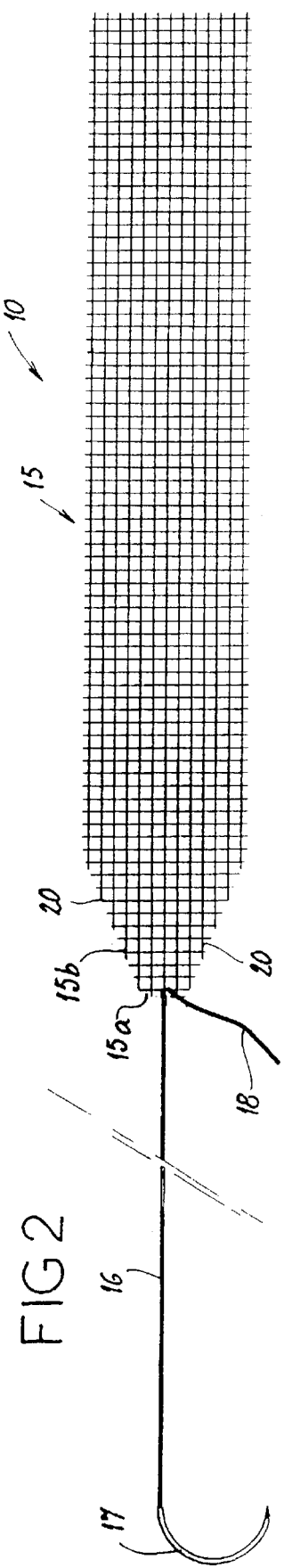

DEVICE FOR TREATING A PROLAPSE BY VAGINAL SUSPENSION

The present invention relates to a device for treating a prolapse by vaginal suspension.

Genital, urinary and rectal prolapses result from a slackening of the tissues supporting the organs, and of the perineum, and cause stress urinary incontinence in elderly women.

Surgical treatment of these prolapses involves connecting one or more of these organs (bladder, vagina, uterus, rectum) to anatomically stable zones, in particular, anteriorly, at Cooper's ligament, on the postero-superior margin of the pubis or, posteriorly, at the area of the promontory, that is to say the antero-superior angle of the sacrum, by "suspending" these organs on these anatomically stable zones.

Surgical treatment of prolapses is presently carried out using nonabsorbable sutures or strengthening strips.

Sutures have the advantage of being easy to put in place during treatment of a prolapse by open surgery, of having a low cost and of having extensive possibilities of use.

However, they have the disadvantage of providing a punctiform and somewhat inelastic fixation of the suspension thread, which is likely to cause shearing of the tissues on which they are placed, leading to rupturing of the anchoring arrangement. The result of this is that their efficacy is limited over time. Moreover, they are complicated to put into place when treating prolapses by laparoscopy, given the need to form numerous knots.

Strips have the advantage of being easy to put into place irrespective of the route employed (open surgery or laparoscopy), of being effective, and of allowing the stresses which are exerted to be distributed at a plurality of anchoring points. They are also capable of rapid incorporation in the anchoring wall and in the surrounding tissues by means of tissue growth.

However, these strips have the disadvantage of having to be twisted when the respective implantation walls are not parallel. The twisted zone acts in scarcely favorable conditions, moving along the band when tension is applied, with the latter becoming thinner at its center, making it difficult to put into place and accentuating the shearing effect. A band of relatively rigid material, such as monofilament polypropylene, has edges which may possibly damage the surrounding tissues along the entire length of the band.

Treatment of a prolapse by vaginal suspension is a delicate operation in view of the relative fragility of the wall of the vagina, and existing devices for performing such suspension, particularly by laparoscopy, are not entirely satisfactory.

The present invention aims to remedy this deficit.

To this end, the device to which the invention relates comprises a unit formed by an elongate part of flexible open-worked material, a suture thread connected to a longitudinal end of said part, and a suture needle connected to this thread; the part has a length which is such that it permits posterior suspension of the vagina at the promontory, that is to say at the antero-superior portion of the sacrum; this part comprises, at its end connected to the suture thread, (i) a distal portion whose width is such that it can cover at least a wide area of the posterior half of the wall of the vagina and it can be sutured very laterally, that is to say in a manner not transfixing the paravagina, and (ii) a rounded cut-out formed in its lateral edge at the distal end, this cut-out having dimensions which are such that it permits engagement of the part around the base of the wall of the vagina, over at least a wide area of the posterior half of this wall, while at the same time leaving the rectum at a sufficient distance so as not to risk compressing the latter; the suture thread is connected to the part in such a way that it is offset laterally in relation to said cut-out.

The device according to the invention is put into place as follows. After inserting optic and surgical trocars, an arciform incision is made in the anterior surface of Douglas' pouch (vaginorectal), then the prerectal fascia is dissected, continuing laterally as far as the posterior fasciculi of the levator muscles, each side of the rectum. A vaginal valve can be fitted to facilitate dissection to the pelvic floor at the level of the sacrosciatic ligament.

The needle is lowered between the vagina and the rectum starting from Douglas' pouch, to the level of the pelvic floor, and is then engaged laterally through the levator muscles in such a way as to ensure a solid point of sliding for the thread; the latter is then slid by pulling on the needle in order to cause the part of open-worked material to descend into the dissected space, until this part positions itself against the posterior surface of the vagina. The cut-out in the distal portion of this part permits wide engagement of this portion around the base of the vagina without compression of the rectum, and the width of this same portion permits contact of the part with the posterior surface of the vagina over a wide area.

The part is then fixed at one side to the pelvic floor by means of the aforementioned thread on the posterior surface of the vagina by successive suturing points as far as the uterosacral ligament with the aid of this same thread. The same maneuvers are repeated on the other side with a second ligature of 25 cm starting from the other distal end of the part.

The part is then fixed to the promontory via its proximal end, to provide the suspension.

Thus, by means of its shape, this part permits distal fixation not to the wall of the vagina but to the levator muscles and the uterosacral ligaments, in other words at stable positions, so as to obtain engagement under optimum conditions.

The open-worked structure of the part makes it possible to limit to the greatest possible extent the risks of exacerbated tissue reaction (fibrosis) and to obtain rapid integration with the tissues by means of these growing through the meshes.

Preferably, the device according to the invention comprises not only the aforementioned unit consisting of the part of open-worked material, the suture thread and the suture needle, intended to be placed at the level of the posterior surface of the vagina, but also a second unit formed by a part of open-worked material, a suture thread and a suture needle, and intended to be placed at the level of the anterior surface of the vagina, to complement the first unit.

This second unit comprises an elongate part of flexible open-worked material, a suture thread connected to a longitudinal end of the part, and a suture needle connected to this thread; said part has a length which is such that it permits an anterior suspension of the vagina at the promontory and comprises, at its end connected to said thread, two oblique lateral edges converging toward each other in the direction of this end, such that the part has a portion which narrows gradually toward this end; the suture thread is connected to this end.

This second unit is put into place as follows. The anterior surface of the vagina is dissected at the level of the vesico-vaginal pouch, then the paravagina is perforated below the adnexa. The needle of this second unit is engaged along the anterior surface of the vagina and engaged through a tissue, as close as possible to the base of this vagina, so as to constitute a stable point of sliding for the thread; the latter is then slid to allow the part to descend along the anterior surface of the vagina. The portion of this part which narrows in the distal direction corresponds to the distal shape of the vesicovaginal pouch, which permits engagement of said part at as far as possible a point, for engagement in a relatively thick and resistant tissue.

Using a running suture with the aid of this same thread, the part made of open-worked material is fixed along one of its edges to the lateral wall of the vagina at the height of the uterine isthmus. The other edge is sutured in an identical manner with a running suture using a second thread of 25 cm in length. In order to avoid transfixing the vagina while at the same time ensuring mechanically satisfactory anchoring, the engagement of the vaginal tissue in the running suture is wide but not very deep.

The part made of open-worked material is then slit longitudinally starting from its proximal end in order to constitute two strands which are engaged each side of the uterine isthmus, below the adnexa, and which are fixed via their proximal portion to the promontory, at the same level as the part ensuring the posterior suspension.

This second unit thus ensures, in a complementary fashion, an anterior suspension of the vagina, and the anterior and posterior suspensions, obtained using the two aforementioned units, together ensure perfect treatment of the prolapse.

Said part of the second unit could be slit at the time of manufacture of said unit instead of being slit by the surgeon during the intervention.

Advantageously, each unit consisting of part of open-worked material, suture thread and suture needle, comprises a strand of suture thread one end of which is connected to the part of open-worked material, in immediate proximity to the end of the suture thread.

This strand makes it easier to form the first knot for fixing the part of open-worked material.

According to a simple embodiment of the invention in this case, the suture thread is simply connected to the part of open-worked material by knotting, and the aforementioned strand consists of a portion of the suture thread continuing beyond the knot.

The part or parts of open-worked material are advantageously formed as a knit of multifilament polyester yarns with square meshes.

This material is particularly suitable for implementing the invention.

Each part is advantageously impregnated with collagen to promote this tissue growth. Their runproof texture permits light engagement so as to utilize all the width of the part. Their wide pores facilitate the passage of the needle.

The suture thread is of conventional type and in particular consists of a braid of polyester yarns. It preferably has a length of the order of 25 cm, required for making a running suture or separate points, and sufficient for not taking up too much space in the confined space imposed by laparoscopy.

The suture needle for its part advantageously has a curved shape sufficient to prevent transfixing upon its introduction on the vaginal wall, and a triangular cross section to facilitate its passage in sometimes thick tissues. It is preferably crimped on the end of the suture thread.

To ensure that it is fully understood, the invention is again described below with reference to the attached diagrammatic drawing which shows, by way of nonlimiting example, a preferred embodiment of the device to which the invention relates:

FIG. 1 is a flat view of a first unit which this device comprises;

FIG. 2 is a flat view of a second unit which this device comprises;

Figure 3:
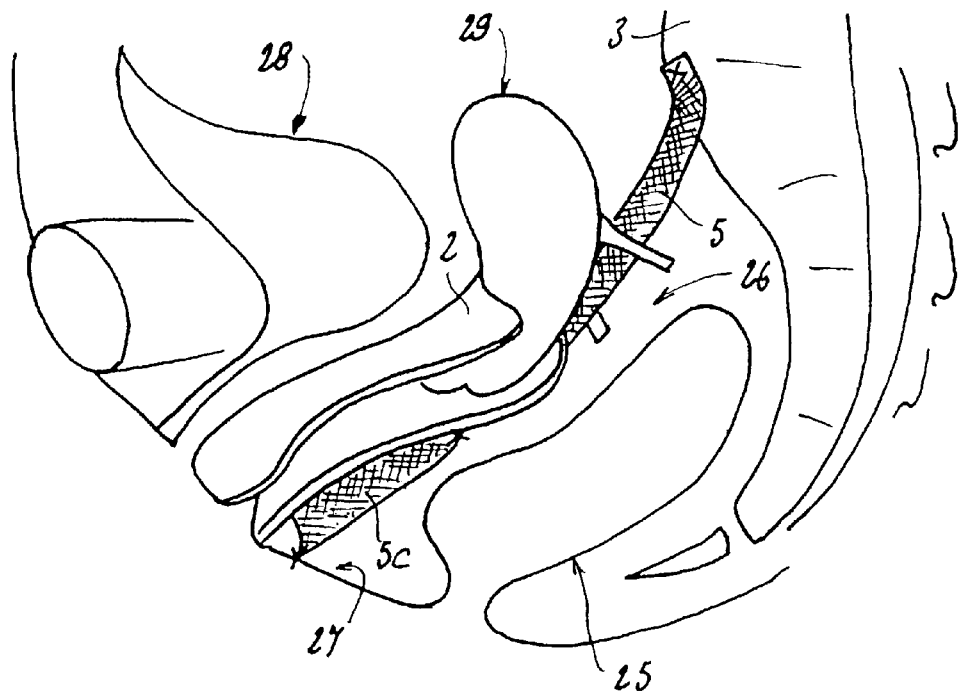
FIG. 3 is a very simplified cross-sectional view of the lower part of a trunk, with said first unit in place.

FIG. 1 illustrates a unit 1 for treating a prolapse by posterior suspension of the vagina 2 at the promontory 3, that is to say the antero-superior angle of the sacrum 4.

This unit 1 comprises:
 a part 5 made of a fabric consisting of multifilament polyester yarns with square meshes, these meshes being approximately two millimeters on their sides,
 a suture thread 6,
 a suture needle 7, and
 a suture strand 8.

The part 5 has a length which is such that it can connect the base of the vagina 2 to the promontory 3. It comprises a proximal part 5a intended to be connected to the promontory 3 and a distal part 5b intended to be connected distally to tissues surrounding the base of the vagina 2.

The proximal part 5a has a sufficient width to ensure resistance of the part 5 to the stresses generated by the suspension.

The distal part 5b has a widened portion 5c, the width of which is greater than the posterior half of the wall of the vagina 2. This portion 5c comprises a cut-out 5d in its distal end edge 5e, widening in the direction of this end edge 5e, the radius of this cut-out 5d corresponding substantially to that of a vagina 2 at its base.

The suture thread 6 consists of a braid of polyester yarns and is knotted to one of the protruding areas 5f of the part 5 which laterally delimit said cut-out 5d. This thread 6 continues beyond the knot 9 which connects it to the part 5 in order to form the aforementioned suture strand 8.

The needle 7 is crimped on the free end of the thread 6 via its proximal end and has a curved shape.

FIG. 2 illustrates a second unit 10 having the same general structure as the unit 1, that is to say comprising:
 a part 15 made of a fabric consisting of multifilament polyester yarns with square meshes, these meshes being two millimeters on their sides,
 a suture thread 16,
 a suture needle 17, and
 a suture strand 18.

The part 15 has a length permitting suspension of the anterior wall of the vagina 2 at the promontory 3, and a sufficient width to ensure its resistance to the stresses generated by the suspension.

This part 15 additionally has two oblique edges 20 at the level of its distal part 15b which converge toward each other in the direction of the distal end 15a of the part 15. This distal part 15b thus has a width which decreases in the direction of this end 15a.

The suture thread 16 is fixed at the level of the median axis of the part 15 to the point of this part 15b by knotting.

This aside, the thread 16, the needle 17 and the strand 18 are in all respects similar to those in the aforementioned unit 1.

As is shown in FIG. 3, the part 5 is intended to be engaged between the vagina 2 and the rectum 25, starting from Douglas' pouch 26, as far as the level of the pelvic floor 27, and to be fixed distally to the levator muscles.

Figure 4:
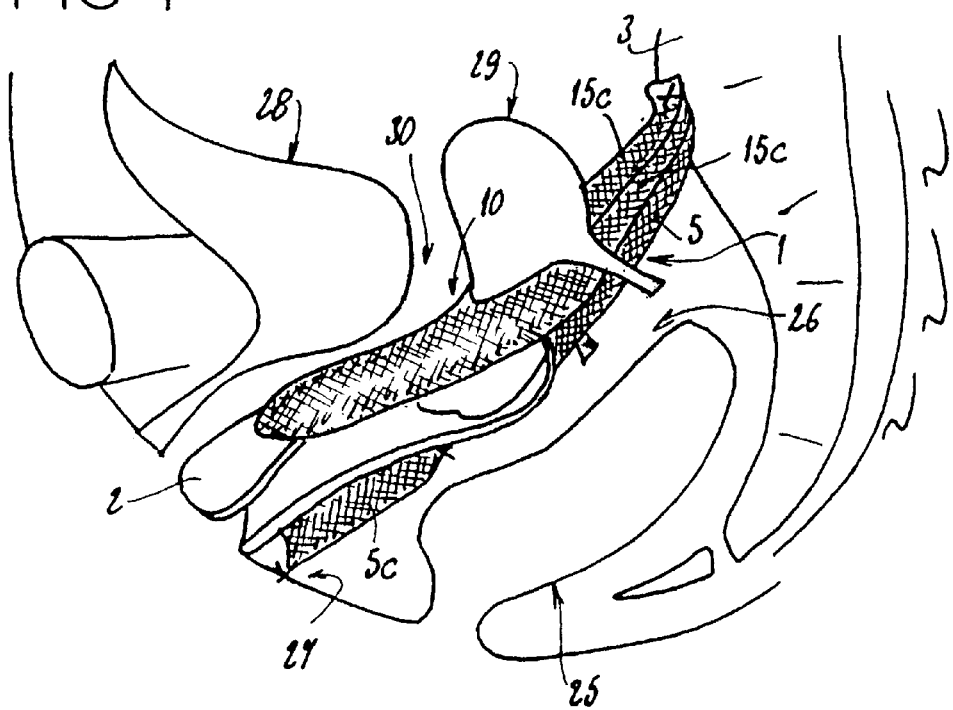
FIG. 4 is a view similar to FIG. 3, with said first and second units in place.

FIG. 4 shows that the part 15 is intended to be engaged between the vagina 2 and the bladder 28 and to be fixed distally to the wall of the vagina 2. This part 15 is additionally intended to be slit longitudinally starting from its proximal edge in order to constitute two strands 15c passing each side of the isthmus of the uterus 29.

More precisely, the device according to the invention is put into place as follows. After inserting optic and surgical trocars, an arciform incision is made in the anterior surface of Douglas' pouch 26 (vaginorectal), then the prerectal fascia is dissected continuing laterally as far as the posterior fasciculi of the levator muscles each side of the rectum 25. A vaginal valve can be fitted to facilitate dissection as far as the pelvic floor 27 at the level of the sacrosciatic ligament.

The needle 7 is lowered between the vagina 2 and the rectum 25 starting from Douglas' pouch 26, to the level of the pelvic floor 27, and is then engaged laterally through a tissue in order to ensure a stable point of sliding for the thread 6; the latter is then slid by pulling on the needle 7 in order to cause the part 5 to descend into the dissected space along the vagina 2, until this part 5 positions itself against the posterior surface of the vagina 5. The cut-out 5d permits wide engagement of the widened distal portion 5c around the base of the vagina 2, and the width of this same portion 5c permits contact of the part 5 with the posterior surface of the vagina over a wide area.

The part 5 is then fixed to the pelvic floor by suturing using the thread 6 and the strand 8 and is then fixed each side of the vagina 2, with suture points formed with the aid of this thread 6.

It is then folded back against the posterior surface of the vagina 2 and is fixed to the uterosacral ligaments.

The anterior surface of the vagina 2 is then dissected at the level of the vesicovaginal pouch 30, then the paravagina is perforated below the adnexa. The needle 17 of the second unit is engaged along the anterior surface of the vagina 2 and engaged through a tissue, as close as possible to the base of this vagina, so as to constitute a stable point of sliding for the thread 6; the latter is then slid to permit the part 15 to descend along the anterior surface of the vagina 2. The distal portion 15b of this part 15 corresponds to the distal shape of the vesicovaginal pouch 30, which permits engagement of said part 15 as far as possible in the distal direction.

The part 15 is then fixed to the wall of the vagina 2, level with the distal portion of the latter, with a running suture which engages widely but not too deeply in the vaginal tissue.

The part 15 is then slit longitudinally starting from its proximal end in order to form the two strands 15c, and these are engaged each side of the uterine isthmus, below the adnexa.

These two strands 15c are then fixed via their proximal portion to the promontory 3 in order to realize the vaginal suspension.

The invention thus makes available a device for treating a prolapse by vaginal suspension which overcomes the disadvantages of the prior art, permitting a posterior distal fixation not to the wall of the vagina but to the pelvic floor and the uterosacral ligaments, that is to say at strong positions, and, in a complementary manner, an anterior distal suspension engaging in a relatively thick and resistant tissue.

What is claimed is:

1. A device for treating a prolapse by vaginal suspension, characterized in that it comprises at least a first unit formed by a first elongate part of a flexible mesh material, a first suture thread connected to a longitudinal end of said first part, and a first suture needle connected to this first thread;

wherein the first part has a length which is such that it permits posterior suspension of the vagina at the promontory, the first part comprises, at the end connected to the first suture thread, (i) a distal portion having a width that can cover at least a wide area of the posterior half of the wall of the vagina and that can be sutured laterally in a manner not transfixing the paravagina, and (ii) a concave rounded cut-out formed in a lateral edge of the distal portion, the concave cut-out widening in the direction of the lateral edge, having a radius that corresponds substantially to the base of the vagina, and having dimensions that permits engagement of the first part around the base of the wall of the vagina, over at least a wide area of the posterior half of the wall, while at the same lime leaving the rectum at a sufficient distance so as not to risk compressing the latter; and the first suture thread is connected to the first part such that the thread is offset laterally in relation to said cut-out.

2. The device as claimed in claim 1, characterized in that it further comprises a second unit intended to be placed at a level of the anterior surface of the vagina to complement the first unit; wherein the second unit comprises a second elongate part of a flexible mesh material, a second suture thread connected to a longitudinal end of the second part, and a second suture needle connected to the second thread;

said second part has a length that permits an anterior suspension of the vagina at the promontory, and comprises, at the end connected to said second thread, two oblique lateral edges converging toward each other in the direction of said end such that the second part has a portion which narrows gradually toward said end; and the second suture thread is connected to said end.

3. The device as claimed in claim 2, characterized in that said second part of the mesh material of the second unit comprises a longitudinal slit extending from its proximal end, thereby constituting two strands, shaped to engage each side of the uterine isthmus, below the adnexa, and to fix via their proximal portion to the promontory.

4. The device as claimed in claim 1, characterized in that said first unit further comprises a first strand of suture thread, wherein one end of the first strand of suture thread is connected to the first part the mesh material, in immediate proximity to the end of the first suture thread that is connected to the first part.

5. The device as claimed in claim 4, characterized in that the first suture thread is connected to the first part of the mesh material by forming a knot, and in that the first suture strand consists of a portion of the first suture thread continuing beyond the knot.

6. The device as claimed in claim 1, characterized in that the first part of the mesh material is formed as a knit of multifilament polyester yarns with square meshes.

7. The device as claimed in claim 1, characterized in that the first part is impregnated with collagen.

8. The device as claimed in claim 1, characterized in that the first suture thread consists of a braid of polyester yarns.

9. The device as claimed in claim 1, characterized in that the first suture thread has a length of the order of 25 cm.

10. The device as claimed in claim 1, characterized in that the first suture needle has a curved shape sufficient to prevent transfixing upon its introduction on the vaginal wall, and a triangular cross section to facilitate its possible passage in thick tissues.

11. The device as claimed in claim 2, characterized in that said first unit further comprises a first strand of suture thread and in that said second unit further comprises a second strand of suture thread, wherein one end of the first strand of suture thread is connected to the first part of the mesh material, in immediate proximity to the end of the first suture thread that is connected to the first part, and wherein one end of the second strand of suture thread is connected to the second part of the mesh material, in immediate proximity to the end of the second suture thread that is connected to the second part.

12. The device as claimed in claim 11, characterized in that the first suture thread is connected to the first part of the mesh material by forming a knot, and in that the first suture strand consists of a portion of the first suture thread continuing beyond the knot, and in that the second suture thread is connected to the second part of the mesh material by forming a knot, and in that the second suture strand consists of a portion of the second suture thread continuing beyond the knot.

13. The device as claimed in claim 2, characterized in that the first part of the mesh material and the second part of the mesh material are each formed as a knit of multifilament polyester yarns with square meshes.

14. The device as claimed in claim 2, characterized in that the first part and the second part are each impregnated with collagen.

15. The device as claimed in claim 2, characterized in that the first suture thread and the second suture thread each consists of a braid of polyester yarns.

16. The device as claimed in claim 2, characterized in that the first suture thread and the second suture thread each have a length of the order of 25 cm.

17. The device as claimed in claim 2, characterized in that the first suture needle and the second suture needle each have a curved shape sufficient to prevent transfixing upon its introduction on the vaginal wall, and a triangular cross section to facilitate its possible passage in thick tissues.

18. The device as claimed in claim 1, characterized in that a radius of the cut-out substantially corresponds to a radius of the base of the wall of the vagina.

* * * * *